US005440641A

United States Patent [19]

Kuusama

[11] Patent Number: 5,440,641

[45] Date of Patent: Aug. 8, 1995

[54] ACTIVE NOISE CANCELLATION SYSTEM

[75] Inventor: Juha Kuusama, Tampere, Finland

[73] Assignee: Nokia Technology GmbH, Pforzheim, Germany

[21] Appl. No.: 14,785

[22] Filed: Feb. 8, 1993

[30] Foreign Application Priority Data

Feb. 14, 1992 [FI] Finland .................................. 920642

[51] Int. Cl.[6] ........................ A61F 11/06; H03B 29/00

[52] U.S. Cl. ........................................................ 381/71

[58] Field of Search .................................... 381/71, 94

[56] References Cited

U.S. PATENT DOCUMENTS 4,677,676 6/1987 Eriksson ................................ 381/71
4,987,598 1/1991 Eriksson ................................ 381/71
5,216,721 6/1993 Melton .................................. 381/71

FOREIGN PATENT DOCUMENTS 2154830 11/1985 United Kingdom .

OTHER PUBLICATIONS

A Multiple Error LMS Algorithm and Its Application to the Active Control of Sound and Vibration, Stephen J. Elliott, vol. ASSP-35, No. 10, Oct. 1987, New York, USA, pp. 1423–1434.

*Primary Examiner*—Curtis Kuntz
*Assistant Examiner*—Ping W. Lee
*Attorney, Agent, or Firm*—Ware, Fressola, Van der Sluys & Adolphson

[57] ABSTRACT

An active noise cancellation system, comprising a circuit for generating one or more reference signals (x(n)) proportional to the noise in the target area, several electronic circuits (1) having adjustable transfer functions (W), such as adaptive filters, adapted to receive the one or more reference signals (x(n)) and to generate noise cancellation signals (y(1,n)), sound sources (2) adapted to receive the noise cancellation signals (y(1,n)) and to generate cancellation noise in the target area for at least partial cancellation of the noise present therein, sensors (3) for detecting residual noise in the target area and converting it to electrical residual noise signals (e(m,n)), transmission path (4) having the estimated transfer function (C') of the transmission path between the electronic circuit (1) and the sensors (3) adapted to receive the one or more reference signals (x(n)), and tuning circuit (5) adapted to receive the residual noise signals (e(m,n)) and output signals from the transmission path circuit (4) and to generate tuning signals (w) and transmit them to the electronic circuit (1) for tuning the transfer functions (W) thereof, and second tuning circuit (6) adapted to receive both the cancellation noise signals (y(1,n)) and the residual noise signals (e(m,n)) and to generate second tuning signals (c) and transmit them to the transmission path circuit (4) for tuning the transfer functions (C') thereof.

1 Claim, 2 Drawing Sheets

ACTIVE NOISE CANCELLATION SYSTEM

TECHNICAL FIELD

The present invention relates to an active noise cancellation system, comprising means for generating one or more reference signals proportional to the noise in the target area, several electronic means having adjustable transfer functions, such as adaptive filters, adapted to receive the reference signal or signals and to generate noise cancellation signals, several sound sources adapted to receive the noise cancellation signals and to generate cancellation noise in the target area for at least partial cancellation of the noise present therein, several sensors for detecting residual noise in the target area and converting it to electrical residual noise signals, transmission path means having the estimated transfer function of the transmission path between each sound source and each sensor adapted to receive the reference signal or signals, and tuning means adapted to receive the residual noise signals and the output signals from the transmission path means and to generate tuning signals and transmit them to the electronic means for tuning the transfer functions thereof.

BACKGROUND OF THE INVENTION

An active noise cancellation system of the kind described above, having several sound sources transmitting noise cancellation signals and several sensors receiving residual noise, has been suggested by S. J. Elliott, I. A. Stothers and P. A. Nelson in their article "A Multiple Error LMS Algorithm and its Application to the Active Control of Sound and Vibration", IEEE Transactions on Acoustics, Speech, and Signal Processing, Vol. ASSP-35, No. 10, October, 1987. A block diagram illustrating such a system is presented also in FIG. 1 of the accompanying drawing, whereto reference will be made in the following.

Let us assume that the system includes L loudspeakers 2 and M microphones 3. A reference signal x(n) is fed to L adaptive filters 1, each having a transfer function W(i,n), by which is meant the transfer function i at time n. In the following, the notation w(i,j,n) means the coefficient j of the transfer function i modelled with an FIR filter at time n. Let the length of these transfer functions be I. The outputs y(k,n) of these filters - - - this is thus the output signal of the transfer function W(k,n) - - - are fed to the L loudspeakers 2. Let the transfer function from loudspeaker i to microphone j be C(i,j,n), and thus its coefficient k at time n is c(i,j,k,n). Let us further model these transfer functions with FIR filters, and let the length of each of these filters be J. The signals from each of the loudspeakers 2 are received by each of the microphones 3. The signal from the m microphone 3 is e(m,n), which is the sum of signals from all loudspeakers 2, plus the unattenuated noise d(m,n). This situation is illustrated in the block diagram of FIG. 2 of the accompanying drawing, where, for clarity, only one of the microphones 3 is shown.

On the basis of the starting assertions presented above, the following equations can be derived:

$$y(k,n) = \sum_{i=0}^{I-1} w(k,i,n)x(n-i) \tag{1}$$

$$e(m,n) = \sum_{l=1}^{L} \sum_{j=0}^{J-1} c(l,m,j,n)y(l,n-j) + d(m,n) \tag{2}$$

-continued $$e(m,n) = \sum_{l=1}^{L} \sum_{j=0}^{J-1} c(l,m,j,n) \sum_{i=0}^{I-1} w(k,i,n-j)x(n-i-j) + d(m,n) \tag{3}$$

If the squares of the expected values of all microphone signals are defined as the total noise $N_{tot}$ in the space in which the noise cancellation signals are adapted to function, that is, in the target area, the following equation is obtained:

$$N_{tot} = E\left\{ \sum_{m=1}^{M} e^2(m,n) \right\} \tag{4}$$

The differential of the total error with respect to the coefficient i of the transfer function W(l,i) is $$\frac{\partial N_{tot}}{\partial w(l,i,n)} = 2E\left\{ \sum_{m=1}^{M} e(m,n) \frac{\partial e(m,n)}{\partial w(l,i,n)} \right\}. \tag{5}$$

Let us assume that W(l,n) and C(l,m,n) are for a moment time-invariant. This means in practice that they are changing only slowly compared with the reference signal x(n) and the residual noise d(m,n). Then the transfer function W(l,n) is denoted as W(l) and the transfer function C(l,m,n) as C(l,m). Correspondingly, the i:th coefficients of said functions are denoted as w(l,i) and c(l,m,i). Differentiating equation 3 gives $$\frac{\partial e(m,n)}{\partial w(l,i)} = \sum_{j=0}^{J-1} c(l,m,j)x(n-i-j). \tag{6}$$

Let us further assume that we have estimates of the transfer functions C(l,m) available, and let us denote these estimates as C'(l,m). If each coefficient w(l,i) of the transfer function W(l) is adjusted at every sample time by a quantity proportional to the negative instantaneous value of the differential given by formula 5, a modified multi-channel filtered-x type algorithm for the coefficient w(l,i,n+l) of the transfer function is obtained, which thus represents the value of said coefficient at a new time n+l.

$$w(l,i,n+1) = w(l,i,n) - \alpha \sum_{m=1}^{M} e(m,n) \sum_{j=0}^{J-1} c'(l,m,j)x(n-i-j), \tag{7}$$

where α is the adaptation coefficient.

The algorithm recounted above has been implemented in a real-time prototype and its performance measured. This has been reported in the above-stated article by Elliott et al. Substantial noise cancellation was only found at the frequency of the reference signal. An essential problem of the algorithm described above and the system based thereon is that fixed transfer functions are used for the estimation of the transmission paths between the loudspeakers and the sensors. In a multi-channel system this entails the need to measure several transfer functions for each installation. For instance, using four loudspeakers and eight sensors requires measurement of the transfer functions of 32 different transmission paths, which for practical reasons is not at all simple. In addition, the use of fixed transfer function estimates makes the system incapable of responding to changes in the acoustics of the target area, such as variations in the number and position of passengers if the target area is a vehicle, variations in temperature and humidity, or changes due to component ageing or failure.

SUMMARY OF THE INVENTION

The object of the present invention is to provide an active noise cancellation system wherein one has succeeded in substantially diminishing the above-stated problems. This object is achieved with the active noise cancellation system of the invention, which is characterized in that the system further comprises second tuning means adapted to receive both the cancellation noise signals and the residual noise signals and to generate second tuning signals and transmit them to the transmission path means for tuning the transfer functions thereof.

The improvement to be achieved with the system of the invention over the previously known system is based on the realization that the transfer functions of the transmission paths need not be measured but they can be estimated when feedback information on the working of the actual system is utilized to assist the estimation. Again, by means of these estimated transfer functions of the transmission paths, the signals producing residual noise signals over said transmission paths to a particular sensor can be estimated. By subtracting the thus estimated residual noise signals from the residual noise received by each sensor, "cleaner" residual noise signals can be obtained for use to tune the transfer functions of the electronic means, such as adaptive filters. In accordance herewith, the transfer functions of the transmission paths can be tuned on the basis of the new value of the coefficient j of the transfer function C'(l,m) to be determined at each new sample time n+1 on grounds of the algorithm $$c'(l,m,j,n+1) = c'(l,m,j,n) + \beta\left[e(m,n) - \sum_{h=1,h\neq 1}^{L}\sum_{k=0}^{J-1} c'(h,m,k,n)y(h,n-k)\right]y(l,n-j),$$

wherein $\beta$ is the adaptation coefficient.

The algorithm presented above can be deduced as follows. First, differentiating the above-stated equation 2 with respect to the coefficient c(l,m,j) we obtain $$\frac{\partial e(m,n)}{\partial c(l,m,j,n)} = y(l,n-j). \tag{8}$$

If the estimated coefficient of the transfer function of the transmission path is denoted as c'(l,m,j), on the basis of equation 8 we obtain an LMS type algorithm to recursively estimate these coefficients $$c'(l,m,j,n+l) = c'(l,m,j,n) + \beta e(m,n)y(l,n-j) \tag{9}$$

However, the algorithm according to equation 9 performs poorly in practice, since the signal e(m,n) used to estimate the transfer function C'(l,m) has correlated noise components in it, namely signals from all other loudspeakers to m:th sensor 3. However, using transfer function estimates according to equation 9, we are able to calculate estimates for these disturbing signals as well, and these can be subtracted from the signal e(m,n) to obtain a "cleaner" residual noise signal for adaptation. In this way, we arrive at the equation already set forth above for calculating a new coefficient c'(l,m,j,n+l)

$$c'(l,m,j,n+1) = c'(l,m,j,n) + \beta\left[e(m,n) - \sum_{h=1,h\neq 1}^{L}\sum_{k=0}^{J-1} c'(h,m,k,n)y(h,n-k)\right]y(l,n-j), \tag{10}$$

BRIEF DESCRIPTION OF THE DRAWINGS

In the following, the system of the invention will be further described with reference to the accompanying drawing, wherein.

BEST MODE FOR CARRYING OUT THE INVENTION

Figures 1, 2:
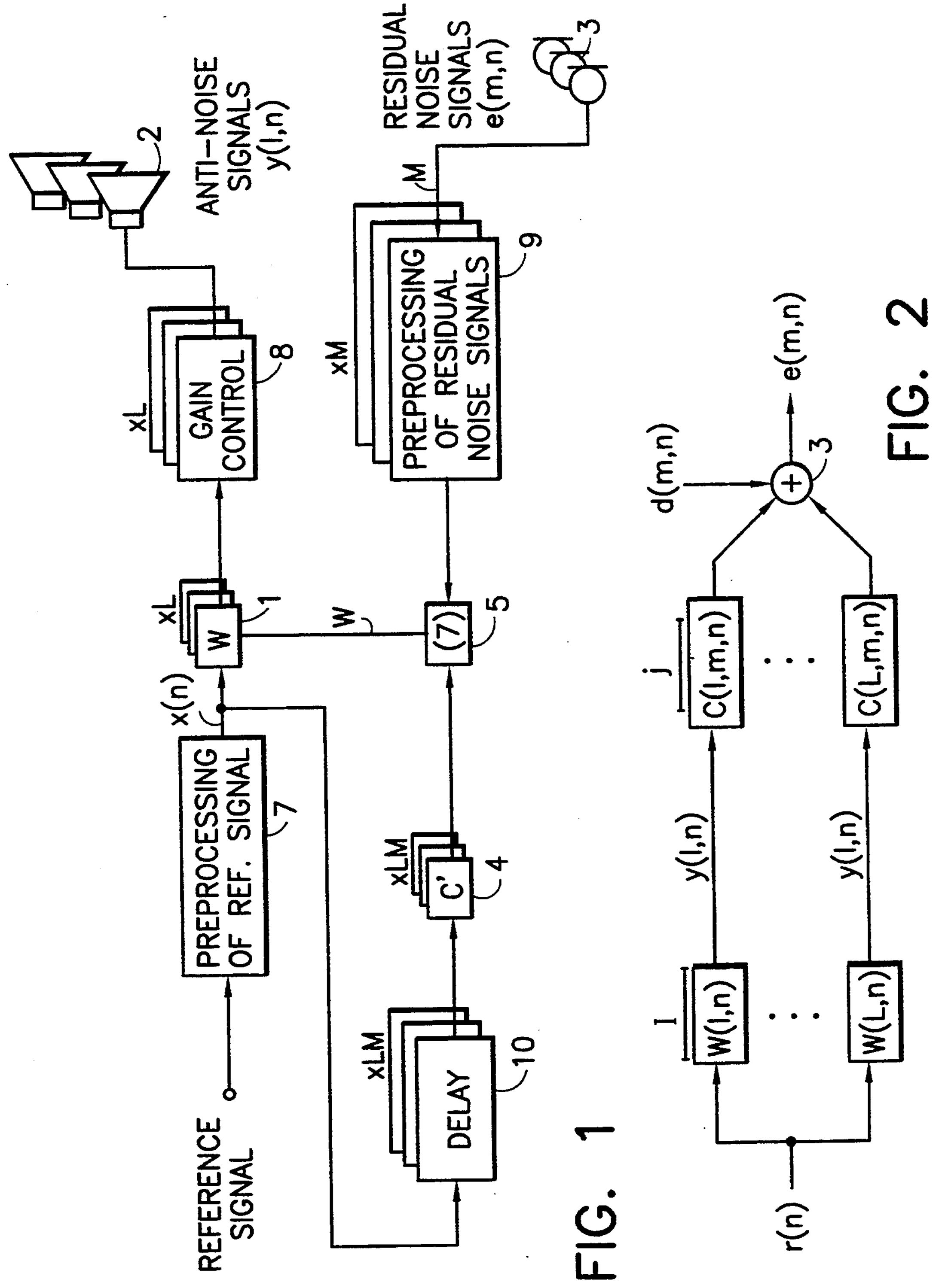
FIG. 1 illustrates an active noise cancellation system of the prior art.
FIG. 2 shows a block diagram illustrating the operation of the system of FIG. 1.

As has already been described in part in the foregoing, FIG. 1 illustrates an active noise cancellation system wherein a reference signal is fed after preprocessing in a reference signal preprocessing means 7 to adaptive filters 1, L of which are provided. The outputs of these filters 1 are fed after amplification in a gain control means 8 to loudspeaker 2, L of which are also provided. These loudspeakers 2 propagate to the target area L noise cancellation signals y(l,n). The effect of these noise cancellation signals is controlled by means of sensors 3, M of which are provided. The residual noise signals e(m,n) received by these sensors 3 are first processed in preprocessing residual noise signals means 9, M of which are provided, and thereafter they are directed to new coefficient transfer function generation means 5. Also the signals derived from fixed transfer function estimation means 4 are fed to new coefficient transfer function generation means 5. Blocks 4 estimate, by means of fixed estimates C', the transfer function of the transmission path between each loudspeaker and each sensor. In accordance with equation 7, a reference signal x is fed to these transfer function estimates of the transmission paths. Said reference signal x is, however, delayed by delays produced both by the adaptive filters 1 and by the actual transmission path, and thus it receives a reference signal from the time n-i-j. These delays are generated by delay means 10. There are L×M of delay means 10 as well as for the transfer function estimates of the transmission paths. The outputs of fixed transfer function estimation means 4 and processing residual noise signals means 9 are combined in new coefficient transfer function generation means 5, which has been adapted in accordance with equation 7 to calculate new values for the transfer functions W of the adaptive filters 1.

Figure 3:
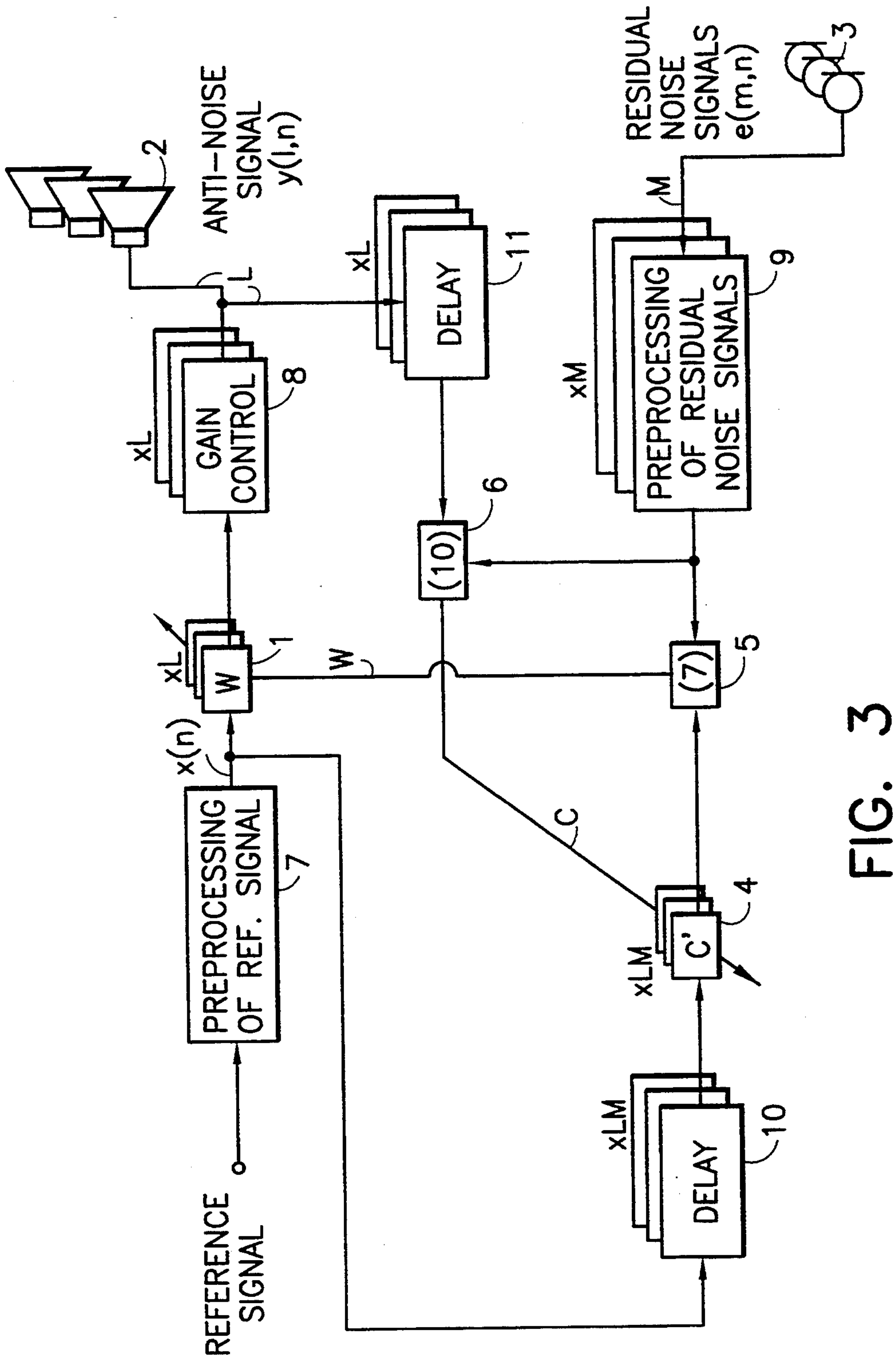
FIG. 3 shows a schematic block diagram of the active noise cancellation system of the invention.

For the reasons stated above, the system of FIG. 1 does not, however, operate in the best possible way, and thus it has been complemented in accordance with the invention so as to achieve a system according to FIG. 3. The blocks corresponding to the system of FIG. 1 have been denoted with similar reference numerals in FIG. 3. This also means that the blocks having similar reference numerals operate exactly in the same way. In contrast to the system of FIG. 1, the system of FIG. 3 comprises a second new coefficient transfer function generation means which is adapted in accordance with the above equation 10 to calculate new transfer function estimates for the transmission paths for use in blocks 4. In accordance with equation 10, is adapted to receive both the noise cancellation signals y(l,n) and the residual noise signals e(m,n). The noise cancellation signals are fed to only after the delay blocks 11. The delays of these blocks 11 correspond to the delay in the transmission path, as in practice the signals of the loudspeakers 2 do not arrive at the sensors until some milliseconds after they have been fed to the loudspeakers 2. In order that this idle time need not be taken into account in, delay blocks 11 are used. On the basis of equation 10, new values for the transfer function estimates for the transmission paths can now be determined in and fed to the blocks 4 for use similarly as in the system of FIG. 1 for adjusting the transfer functions W of the adaptive filters 1.

In the foregoing, the system of the invention has been described only by means of one exemplary embodiment, and it will be appreciated that the system according to the invention can be achieved with very many different apparatus arrangements without its operation departing from the operation of the system defined in the appended claims.

I claim:

1. An active noise cancellation system, comprising:

means for generating one or more reference signals (x(n)) proportional to noise in a target area;

electronic means (1) having adjustable transfer functions (W), including adaptive filters, to receive the one or more reference signals (x(n)) and to generate noise cancellation signals (y(l,n));

a plurality of sound sources (2) to receive the noise cancellation signals (y(l,n)) and to generate cancellation noise in the target area for at least partial cancellation of the noise present therein;

a plurality of sensors (3) for detecting residual noise in the target area and converting it to electrical residual noise signals (e(m,n));

transmission path means having an estimated transfer function (c') of the transmission path between each of the plurality of sound sources (2) and each of the plurality sensors (3), to receive the one or more reference signals (x(n)) and to provide output signals;

tuning means (5) to receive the electrical residual noise signals (e(m,n) and the output signals from the transmission path means (4) and to generate tuning signals (w) and transmit them to the electronic means (1) for tuning the adjustable transfer function (W) thereof; and second tuning means (6) to receive both the cancellation noise signals (y(l,n)) and the residual noise signals (e(m,n)) and to generate second tuning signals (c) and feed them back to the transmission path means (4) for tuning the estimated transfer functions (C') thereof, where l is a coefficient for L sound sources (2), m is a coefficient for M sensors (3), and n is a coefficient for time in the transfer functions, the second tuning means (6) generating the second tuning signals (c) in response to new values (c'(l,m,j,n+1), which are determined by an algorithm, where c'(l, m, j, n+1)=c'(l, m, j, n)+

$$\beta\left[e(m,n) - \sum_{h=1,h\neq 1}^{L}\sum_{k=0}^{J-1} c'(h,m,k,n)y(h,n-k)\right]y(l,n-j),$$

wherein $\beta$ is an adaptation coefficient, where j is a the coefficient of the transfer function i modeled with an FIR filter at time n, J is the length of the FIR filter used to model the transfer function, h is a coefficient of the transfer function at time n.

* * * * *

UNITED STATES PATENT AND TRADEMARK OFFICE

CERTIFICATE OF CORRECTION

PATENT NO. : 5,440,641

DATED : August 8, 1995

INVENTOR(S) : J. Kuusama

It is certified that error appears in the above-indentified patent and that said Letters Patent is hereby corrected as shown below:

column 6, line 6, after "means", please insert --(4)--; and at line 13, please change "(e(m,n)" to --(e(m,n))--.

Signed and Sealed this

Twelfth Day of December, 1995

Attest:

Bruce Lehman

BRUCE LEHMAN

*Attesting Officer*

*Commissioner of Patents and Trademarks*